(12) United States Patent
Yoshinaga

(10) Patent No.: US 11,712,722 B2
(45) Date of Patent: Aug. 1, 2023

(54) KITCHEN GARBAGE TREATMENT MATERIAL AND METHOD FOR MANUFACTURING THE SAME, AND KITCHEN GARBAGE TREATMENT METHOD

(71) Applicant: DAIKI CO., LTD., Tokyo (JP)

(72) Inventor: Junji Yoshinaga, Tokyo (JP)

(73) Assignee: DAIKI CO., LTD., Tokyo (JP)

( * ) Notice: Subject to any disclaimer, the term of this patent is extended or adjusted under 35 U.S.C. 154(b) by 514 days.

(21) Appl. No.: 16/911,886

(22) Filed: Jun. 25, 2020

(65) Prior Publication Data
US 2020/0324325 A1 Oct. 15, 2020

Related U.S. Application Data

(63) Continuation of application No. PCT/JP2018/041607, filed on Nov. 9, 2018.

(30) Foreign Application Priority Data

Jan. 22, 2018 (JP) .................................. 2018-008187

(51) Int. Cl.
| | | |
|---|---|---|
| B09B 3/10 | (2022.01) | |
| B01J 20/26 | (2006.01) | |
| B29B 17/02 | (2006.01) | |
| B29B 17/04 | (2006.01) | |

(52) U.S. Cl.
CPC .................. *B09B 3/10* (2022.01); *B01J 20/26* (2013.01); *B29B 17/02* (2013.01); *B29B 17/04* (2013.01)

(58) Field of Classification Search
None
See application file for complete search history.

(56) References Cited

U.S. PATENT DOCUMENTS

| | | | |
|---|---|---|---|
| 9,393,546 B2 * | 7/2016 | Ito | ........................... B29B 17/02 |
| 10,071,362 B2 * | 9/2018 | Ito | ........................... B01J 20/30 |
| 2015/0360200 A1 * | 12/2015 | Ito | ........................... B01J 20/22 |
| | | | 502/401 |
| 2015/0360202 A1 * | 12/2015 | Ito | ........................... B01J 20/26 |
| | | | 252/194 |

(Continued)

FOREIGN PATENT DOCUMENTS

| | | |
|---|---|---|
| JP | S61-125436 A | 6/1986 |
| JP | S63-192446 A | 8/1988 |
| JP | H08-276171 A | 10/1996 |

(Continued)

OTHER PUBLICATIONS

Jan. 29, 2019 Search Report issued in International Patent Application No. PCT/JP2018/041607.

(Continued)

*Primary Examiner* — Joseph D Anthony
(74) *Attorney, Agent, or Firm* — Oliff PLC (57) ABSTRACT

A kitchen garbage treatment material absorbs moisture contained in kitchen garbage, and is constituted by grains. The grains contain a water-absorbent material. The water-absorbent material is constituted by at least one of fluff pulp and water-absorbent polymer that have been obtained by separating plastic from a sanitary product that contains the plastic, the fluff pulp, and the water-absorbent polymer.

10 Claims, 5 Drawing Sheets

(56) References Cited

U.S. PATENT DOCUMENTS

2015/0360203 A1\* 12/2015 Ito .......................... B02C 23/10
  502/402
2020/0324325 A1\* 10/2020 Yoshinaga ................ B09B 5/00

FOREIGN PATENT DOCUMENTS

| JP | 2009-226233 A | 10/2009 |
|----|---------------|---------|
| WO | 2014/181469 A1 | 11/2014 |

OTHER PUBLICATIONS

Jan. 29, 2019 Written Opinion issued in International Patent Application No. PCT/JP2018/041607.

\* cited by examiner

KITCHEN GARBAGE TREATMENT MATERIAL AND METHOD FOR MANUFACTURING THE SAME, AND KITCHEN GARBAGE TREATMENT METHOD

CROSS REFERENCE TO RELATED APPLICATION

This is a Continuation of International Application No. PCT/JP2018/041607 filed Nov. 9, 2018, which claims the benefit of Japanese Application No. 2018-008187 filed Jan. 22, 2018. The contents of these applications are hereby incorporated by reference in their entirety.

TECHNICAL FIELD

The present invention relates to a kitchen garbage treatment material and method for manufacturing the same, and a kitchen garbage treatment method.

BACKGROUND ART

Patent Document 1 describes a kitchen garbage treatment device that treats kitchen garbage. The kitchen garbage treatment device described in Patent Document 1 includes a storage container that stores kitchen garbage, and a heating means that is provided in an upper portion of the storage container. The heating means is constituted by a heater for drying or the like, and heats the kitchen garbage. The kitchen garbage treatment device treats kitchen garbage by using the heating means to heat and dry the kitchen garbage stored in the storage container.

CITATION LIST

Patent Document
 Patent Document 1: JP 2009-226233A

SUMMARY OF INVENTION

Technical Problem

The kitchen garbage treatment device described above can remove moisture, which is a cause of foul odor, in the kitchen garbage and can thus suppress the emission of foul odors from kitchen garbage. However, a problem with this kitchen garbage treatment device is that a heater for drying is used, and therefore kitchen garbage cannot be treated without a power source.

Solution to Problem

The present invention was created in view of the problem described above, and an object thereof is to provide a kitchen garbage treatment material and method for manufacturing the same, and a kitchen garbage treatment method with which kitchen garbage can be treated without a power source.

A kitchen garbage treatment material according to the present invention is a kitchen garbage treatment material that absorbs moisture contained in kitchen garbage, the kitchen garbage treatment material including a powder or a grain containing a water-absorbent material constituted by at least one of fluff pulp and water-absorbent polymer obtained by separating plastic from a sanitary product that contains the plastic, the fluff pulp, and the water absorbent polymer.

This kitchen garbage treatment material is constituted by a powder or a grain containing a water-absorbent material constituted by at least one of fluff pulp and water-absorbent polymer obtained by separating plastic from a sanitary product, and absorbs moisture contained in kitchen garbage. This makes it possible to remove moisture from the kitchen garbage and treat the kitchen garbage without needing a power source.

A method for manufacturing a kitchen garbage treatment material that absorbs moisture contained in kitchen garbage according to the present invention is a method that includes: a preparing step of preparing a water-absorbent material that is constituted by at least one of fluff pulp and water-absorbent polymer obtained by separating plastic from a sanitary product that contains the plastic, the fluff pulp, and the water-absorbent polymer; and a forming step of forming the kitchen garbage treatment material that is constituted by a powder or a grain that contains the water-absorbent material prepared in the preparing step.

In this manufacturing method, a kitchen garbage treatment material is formed that is constituted by a powder or a grain containing a water-absorbent material constituted by at least one of fluff pulp and water-absorbent polymer obtained by separating plastic from a sanitary product, and absorbs moisture contained in the kitchen garbage. Thus, with the manufactured kitchen garbage treatment material, it is possible to remove moisture in kitchen garbage and treat the kitchen garbage without needing a power source.

Also, a method of treating kitchen garbage according to the present invention includes: causing the kitchen garbage treatment material described above to absorb moisture contained in the kitchen garbage, by causing the kitchen garbage treatment material to come into contact with the kitchen garbage.

In this treatment method, moisture contained in kitchen garbage is absorbed by the kitchen garbage treatment material described above. This makes it possible to remove moisture from the kitchen garbage and treat the kitchen garbage without needing a power source.

Advantageous Effects of Invention

With the present invention, a kitchen garbage treatment material and method for manufacturing the same, and a kitchen garbage treatment method are realized with which kitchen garbage can be treated without a power source.

DESCRIPTION OF EMBODIMENTS

The following is a detailed description of an embodiment of the present invention with reference to the drawings. Note that in the descriptions of the diagrams, the same reference numerals are used for the same elements and redundant descriptions thereof are omitted.

Figure 1:
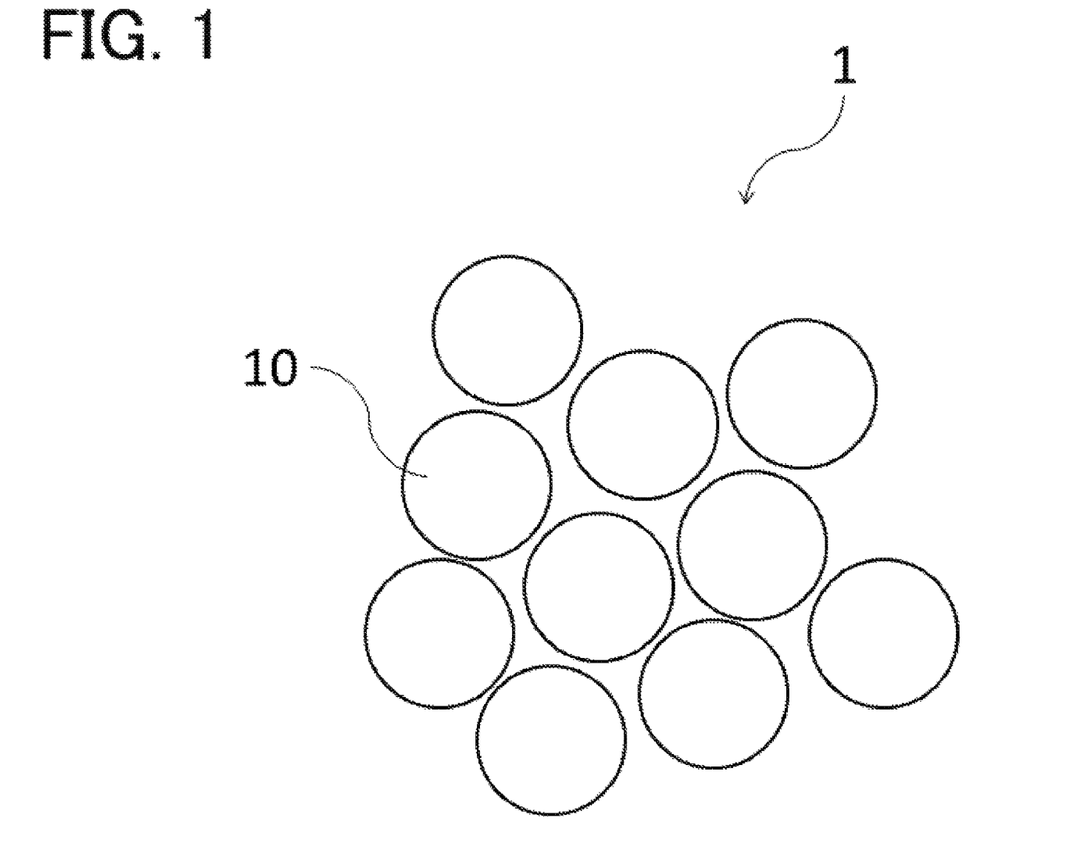
FIG. 1 is a schematic diagram showing an embodiment of a kitchen garbage treatment material according to the present invention.

FIG. 1 is a schematic diagram showing an embodiment of a kitchen garbage treatment material according to the present invention. A kitchen garbage treatment material 1 absorbs moisture contained in kitchen garbage and is constituted by a plurality of grains 10. The grain diameter of each of the grains 10 may be around 3 to 15 mm, for example.

The grains 10 contain a water-absorbent material and are water-absorbent. The water-absorbent material is constituted by at least one of fluff pulp and water-absorbent polymer originating from a sanitary product. That is to say that the grains 10 may also contain only one of fluff pulp and water-absorbent polymer, and may also contain both.

The fluff pulp and the water-absorbent polymer are specifically obtained by separating plastic from a sanitary product that includes plastic, fluff pulp, and water-absorbent polymer (including highly water-absorbent polymer; same below). This separation can be performed with a commonly-known separating device (a classifying device). The sanitary product may be, for example, a diaper, a sanitary napkin, or a urine-absorbing pad. It is preferable to use a sanitary product that is a waste product.

Note that it is difficult to completely separate plastic from sanitary products, and therefore fluff pulp after separation may have plastic pieces attached thereto. It is preferable that the weight ratio of plastic pieces to fluff pulp is 5% or less.

Figure 2:
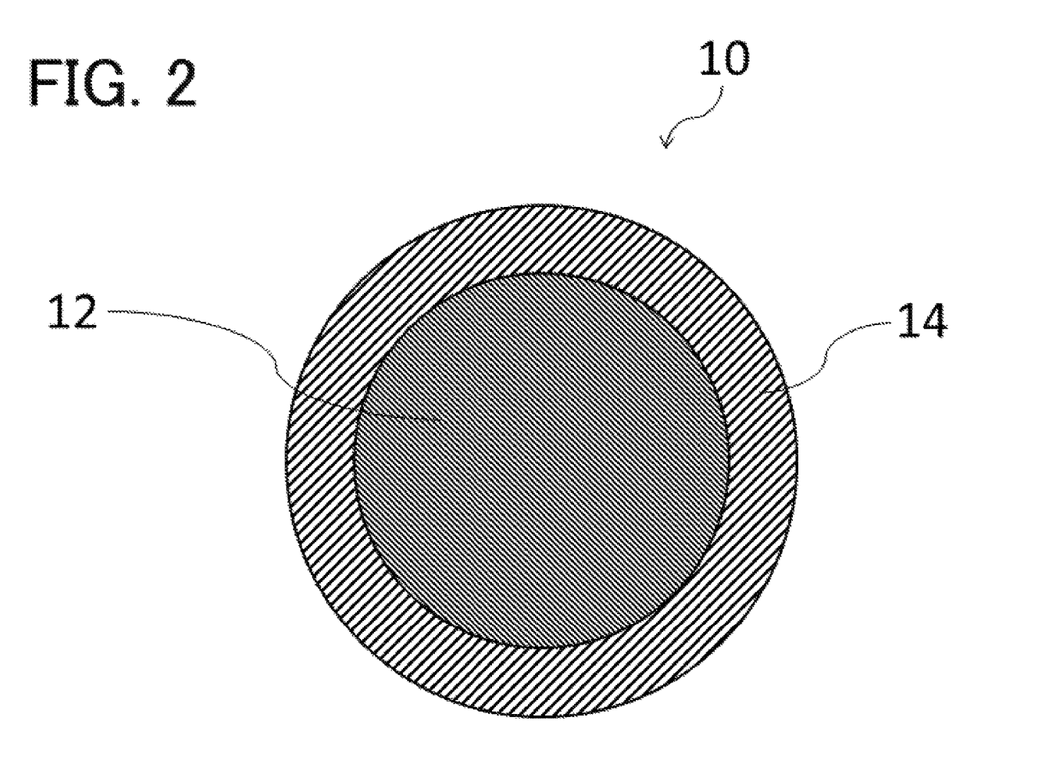
FIG. 2 is a sectional view showing a grain 10.

FIG. 2 is a sectional view showing a grain 10. Each grain 10 includes a granule 12 (core portion), and a coating portion 14. The granule 12 is obtained from a granulating material (material that constitutes the granule 12) containing the water-absorbent material being granulated. The granule 12 is formed into a granular shape. The granular shape may be, for example, spherical, cylindrical, elliptical, or the like. The granule 12 has the function of absorbing and retaining moisture contained in kitchen garbage. The granule 12 (granulating material) may contain the water-absorbent material only, or may contain the water-absorbent material and other materials. The granule 12 may also contain, for example, a binder as another material. CMC (carboxymethyl-cellulose), PVA (polyvinyl alcohol), or dextrin can be used as the binder, for example.

The coating portion 14 is provided so as to coat the granule 12. The coating portion 14 may coat the entire surface of the granule 12, or may coat only a portion thereof. The coating portion 14 has the function of bonding a plurality of the grains 10, which have absorbed moisture contained in kitchen garbage, to each other. The coating portion 14 contains a bonding material that becomes viscous when moisture is absorbed. Water-absorbent polymer can be used as the bonding material, for example. The water-absorbent polymer may be water-absorbent polymer originating from sanitary products (water-absorbent polymer that constitutes the water-absorbent material), or may be water-absorbent polymer not originating from sanitary products. The coating portion 14 may also contain the water-absorbent material, or may also not contain the water-absorbent material.

The kitchen garbage treatment material 1 (the grains 10) preferably includes the water-absorbent material as the primary material thereof. Here, the primary material of the kitchen garbage treatment material 1 is defined as the material that has the largest percentage of weight in the kitchen garbage treatment material 1, out of the materials that constitute the kitchen garbage treatment material 1. Also, it is preferable that the kitchen garbage treatment material 1 is constituted by organic matter only. That is to say that if the kitchen garbage treatment material 1 contains other materials in addition to the water-absorbent material, it is preferable that all other materials are organic matter.

The kitchen garbage treatment material 1 may also contain a deodorizing material or an odor-removing material. The kitchen garbage treatment material 1 may also contain an aromatic material. The deodorizing material, odor-removing material, and aromatic material may be contained in either one of the granule 12 or the coating portion 14 only, or may be contained in both.

Next, an example of a method for manufacturing the kitchen garbage treatment material 1 will be described as an embodiment of the method for manufacturing the kitchen garbage treatment material according to the present invention. This manufacturing method is a method for manufacturing the kitchen garbage treatment material 1, and includes a preparing step and a forming step.

The preparing step is a step of preparing the water-absorbent material. That is to say that in the preparing step, a water-absorbent material is prepared that is constituted by at least one of fluff pulp and water absorbent polymer that have been obtained by separating plastic from a sanitary product that contains plastic, fluff pulp, and water-absorbent polymer. In the preparing step, the water-absorbent material may be created by separating plastic from sanitary products with the use of a separating device, or a pre-created water-absorbent material may be procured.

The forming step is a step of forming the kitchen garbage treatment material 1 that is constituted by a plurality of the grains 10 that contain the water-absorbent material prepared in the preparing step. The forming step includes a granulating step and a coating step. The granulating step is a step of forming the granules 12 that constitute the grains 10 by granulating a granulating material that contains the water-absorbent material. An extrusion granulator, for example, can be used to granulate the granulating material. A plurality of granules 12 are formed in the granulating step. Prior to granulation, the granulating material is subjected to pretreatment as necessary, such as pulverization, kneading, and hydration.

The coating step is a step of forming the coating portions 14 so as to coat the granules 12. In order to form the coating portions 14, it is sufficient that a powdery coating material (material that constitutes the coating portion 14) is attached to the surface of the granules 12. A coating device, for example, can be used to attach the coating material. Then, post-processing such as sifting (sizing), drying, and the like is performed as necessary. The kitchen garbage treatment material 1 that is constituted by a plurality of grains 10 is obtained as described above.

Figure 3:
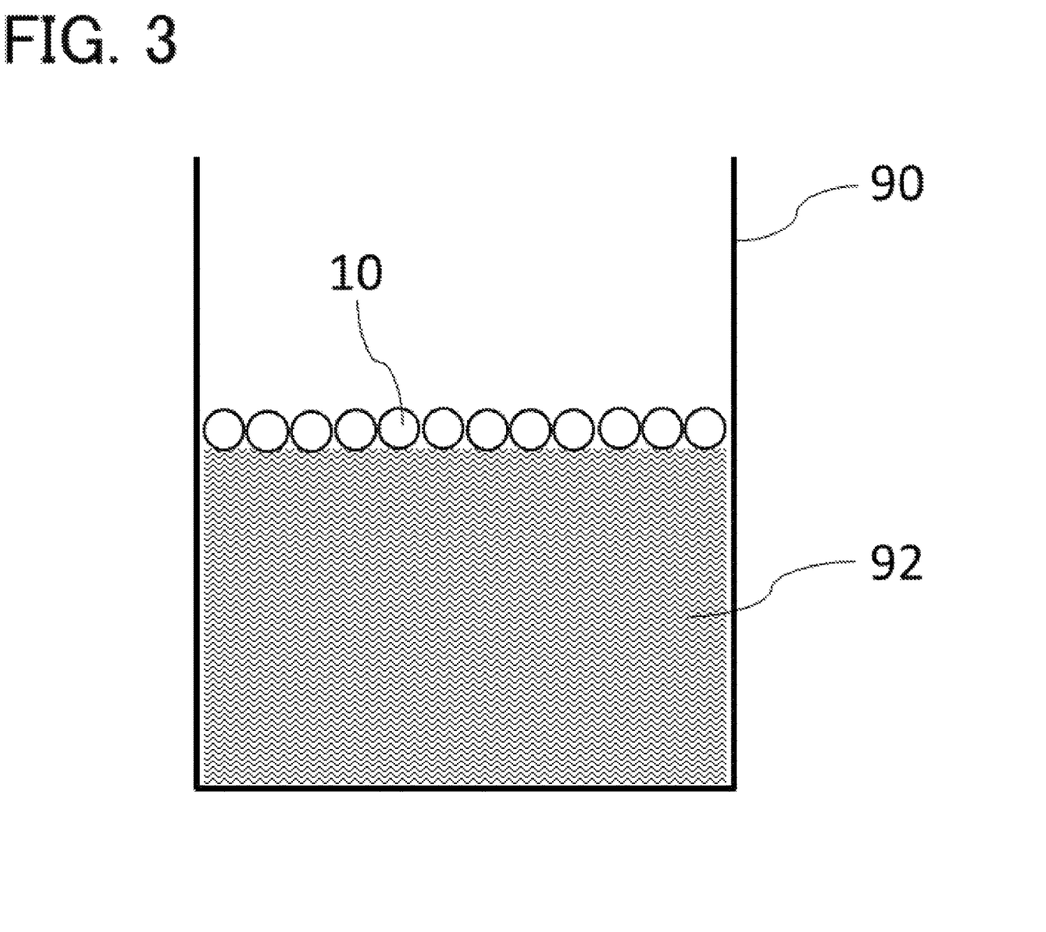
FIG. 3 is a schematic diagram showing the state of a kitchen garbage treatment material 1 during use.

An example of a method of using the kitchen garbage treatment material 1 will be described as an embodiment of a kitchen garbage treatment method according to the present invention, with reference to FIG. 3. The method of treating kitchen garbage includes causing the kitchen garbage treatment material 1 to absorb moisture contained in kitchen garbage, by causing the kitchen garbage treatment material 1 to come into contact with the kitchen garbage. In FIG. 3, the kitchen garbage treatment material 1 is in contact with kitchen garbage 92 due to the kitchen garbage treatment material 1 (a plurality of the grains 10) being spread onto the kitchen garbage 92 that has been discarded in a garbage bin 90. At this time, the kitchen garbage 92 and the grains 10 may also be mixed together by stirring the kitchen garbage 92. In this way, it is possible to remove moisture, which is a cause of foul odors, in the kitchen garbage 92 and thus treat the kitchen garbage 92 by causing the kitchen garbage treatment material 1 to come into contact with the kitchen garbage 92. Thus, it is possible to suppress the emission of foul odors from the kitchen garbage 92.

The following describes the effects of the present embodiment. In the present embodiment, the kitchen garbage treatment material 1 is formed that is constituted by the grains 10 that contain the water-absorbent material constituted by at least one of fluff pulp and water-absorbent polymer obtained by separating plastic from a sanitary product, and absorbs moisture contained in kitchen garbage. In the treatment method described above, moisture contained in kitchen garbage is actually absorbed by the kitchen garbage treatment material 1. For this reason, according to the present embodiment, it is possible to remove moisture in kitchen garbage and thus treat the kitchen garbage without needing a power source. Accordingly, the kitchen garbage treatment material 1 and manufacturing method thereof, and a kitchen garbage treatment method are realized with which kitchen garbage can be treated without a power source.

With the kitchen garbage treatment material 1, it is possible to easily treat kitchen garbage in a variety of places. For example, it is not only easy to treat household kitchen garbage, but also kitchen garbage produced during food preparation at eateries, kitchen garbage that is disposed of in garbage bins in tearooms, cafes, and the like, and kitchen garbage that is disposed of in garbage bins that are set up next to vending machines.

Also, the water-absorbent material that is used is constituted by at least one of fluff pulp and water-absorbent polymer originating from a sanitary product, and therefore it is possible to obtain the water-absorbent material from the waste material of sanitary products. Thus, it is possible to reduce the cost of procuring material and therefore reduce the cost of manufacturing the kitchen garbage treatment material 1. The sanitary product being a paper diaper is particularly advantageous for obtaining a large amount of fluff pulp and water-absorbent polymer from a single sanitary product. Furthermore, with the kitchen garbage treatment material 1, it is possible to treat kitchen garbage without needing a dedicated container. That is to say that it is possible to treat kitchen garbage as is, without transferring kitchen garbage disposed of in a garbage bin or the like to a dedicated container.

The kitchen garbage treatment material 1 is constituted by a plurality of the grains 10. In this case, unlike a case in which the kitchen garbage treatment material 1 is constituted by a powder, the kitchen garbage treatment material 1 is unlikely to scatter. This is advantageous as the kitchen garbage treatment material 1 becomes easier to handle. Also, compared to a case in which the kitchen garbage treatment material 1 is constituted by a powder, this is advantageous as the kitchen garbage treatment material 1 that has been used (kitchen garbage treatment material 1 that has absorbed moisture) can be easily removed.

The grains 10 include granules 12 that are obtained by granulating a granulating material that contains the water absorbent material. In the granule 12, moisture is not only absorbed by the water-absorbent material itself, but is also absorbed through gaps between the water-absorbent material. Thus, it is possible to increase the water absorbency of the grains 10 and therefore increase the water absorbency of the kitchen garbage treatment material 1.

Figure 4:
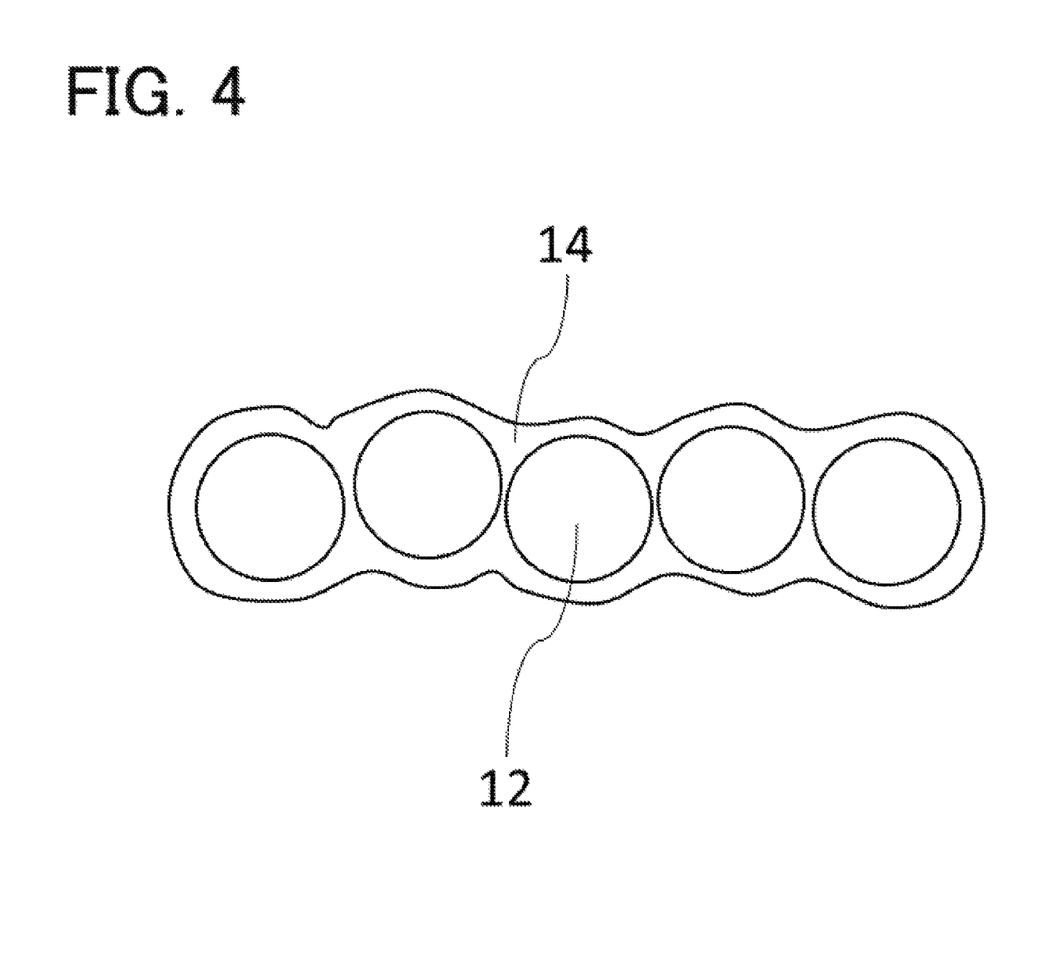
FIG. 4 is a diagram for illustrating the effects of the kitchen garbage treatment material 1.

The grains 10 include the coating portions 14 that have the function of binding a plurality of the grains 10, which have absorbed moisture, to each other. For this reason, after the kitchen garbage treatment material 1 is used, as shown in FIG. 4, the plurality of the grains 10 that have absorbed moisture form a cluster. Thus, the kitchen garbage treatment material 1 can be much more easily removed after use.

The primary material of the kitchen garbage treatment material 1 being the water-absorbent material is advantageous for reducing the cost of procuring materials and increasing the water-absorbency of the kitchen garbage treatment material 1. Also, if the material of the kitchen garbage treatment material 1 is organic matter only, the kitchen garbage treatment material 1 can be obtained that is suitable for incineration. If the kitchen garbage treatment material 1 is suitable for incineration in this way, the kitchen garbage treatment material 1 can be disposed of as burnable garbage after use, which therefore increases convenience for the user.

In the case in which the kitchen garbage treatment material 1 contains a deodorizing material or an odor-removing material, even if kitchen garbage emits a foul odor, the foul odor can be mitigated. In the case in which the kitchen garbage treatment material 1 contains an aromatic material, even if kitchen garbage emits a foul odor, the foul odor can be masked.

The present invention is not limited by the embodiment described above, and various variations thereof are possible. In the embodiment described above, an example is given in which the grains 10 have a multi-layered structure that is constituted by the granule 12 and the coating portion 14. However, it is not absolutely necessary to provide the coating portion 14. That is to say that the grains 10 may also have a single-layered structure that is constituted by the granule 12 only.

Figure 5:
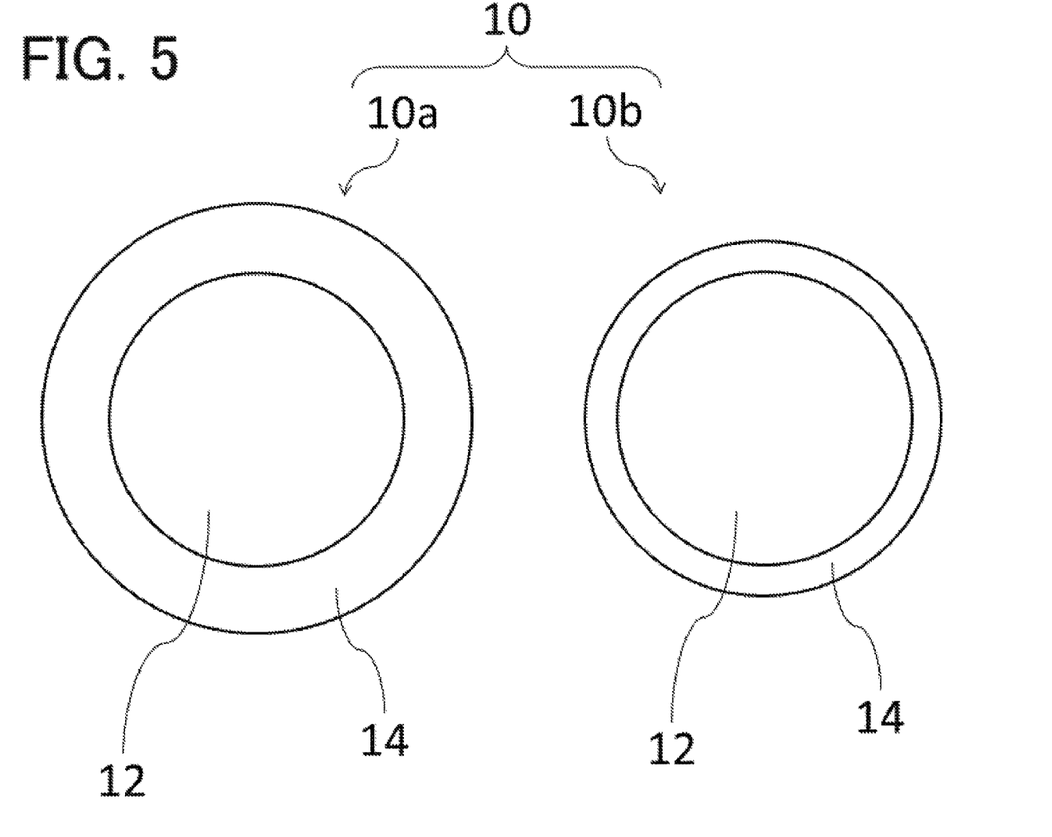
FIG. 5 is a diagram for illustrating a variation of the grains 10.

In the embodiment described above, an example is given in which the coating portions 14 of the plurality of grains 10 are of equal thicknesses. However, as shown in FIG. 5, the plurality of grains 10 may also include grains 10a (first grains) of which the coating portions 14 thereof are relatively thick, and grains 10b (second grains) of which the coating portions 14 thereof are relatively thin. The thickness of the coating portions 14 of the grains 10b is preferably no more than 80% of the thickness of the coating portions 14 of the grains 10a, and more preferably no more than 50% of the thickness of the coating portions 14 of the grains 10a. The granules 12 of the grains 10a and the granules 12 of the grains 10b are constituted by a material of the same composition. The coating portions 14 of the grains 10a and the coating portions 14 of the grains 10b are constituted by a material of the same composition. Also, the granules 12 of the grains 10a and the granules 12 of the grains 10b have substantially the same shape and size.

In this case, a first coating step and a second coating step are included in the coating step. The first coating step is a step of forming the coating portion 14 to be relatively thick on some of the granules 12 of the plurality of granules 12 that are formed in the granulating step. The grains 10a are obtained in this step. Also, the second coating step is a step of forming the coating portions 14 to be relatively thin on the remaining granules 12 of the plurality of granules 12 that are formed in the granulating step. The grains 10b are obtained in this step.

Incidentally, as described above, the coating portions 14 contribute to the formation of clusters constituted by the grains 10 that have been used. On the other hand, the coating portions 14 are provided so as to coat the granules 12, and therefore hinder moisture from quickly reaching the granules 12. Here, moisture can quickly reach the granules 12 of the grains 10b because the coating portions 14 of the grains 10b is made thinner. Also, the bonding effect of the coating portions 14 of the grains 10a extends to the grains 10b in the periphery of the grains 10a. For this reason, even if the coating portions 14 of the grains 10b are thin, it is possible to ensure a suitable cluster strength in relation to the formation of clusters of the grains 10 that have been used. In this way, providing the plurality of grains 10a and 10b, of which the thicknesses of the coating portions 14 thereof varies, is advantageous for suppressing the degradation of water absorption of the kitchen garbage treatment material 1 while ensuring the suitable cluster strength of the grains 10 that have been used.

In the embodiment described above, an example is given in which the kitchen garbage treatment material 1 is constituted by grains (the grains 10). However, the kitchen garbage treatment material 1 may also be constituted by a powder that contains the water-absorbent material. In this case, unlike a case in which the kitchen garbage treatment material 1 is constituted by grains, there is no need to form the water-absorbent material into a granular shape. For this reason, it is possible to simplify the manufacturing steps of the kitchen garbage treatment material 1.

LIST OF REFERENCE NUMERALS

1 Kitchen garbage treatment material
10 Grain
10a Grain (first grain)
10b Grain (second grain)
12 Granule
14 Coating portion
90 Garbage bin
92 Kitchen garbage

The invention claimed is:

1. A kitchen garbage treatment material that absorbs moisture contained in kitchen garbage, the kitchen garbage treatment material comprising:
a plurality of grains containing a water-absorbent material constituted by at least one of fluff pulp and water-absorbent polymer obtained by separating plastic from a sanitary product that contains the plastic, the fluff pulp, and the water-absorbent polymer,
wherein the grains include a granule that is obtained by granulating a granulating material that contains the water-absorbent material, and a coating portion that is provided so as to coat the granule and functions to bond the plurality of grains, which have absorbed moisture, to each other, and
wherein the plurality of grains include both a first grain and a second grain, wherein the coating portion of the first grain is thicker than the coating portion of the second grain such that a thickness of the coating portion of the second grain is 80% or less of a thickness of the coating portion of the first grain.

2. The kitchen garbage treatment material according to claim 1,
wherein the coating portion of the first grain and the coating portion of the second grain are constituted by a material of the same composition.

3. The kitchen garbage treatment material according to claim 1,
wherein the kitchen garbage treatment material includes the water-absorbent material as a primary material.

4. The kitchen garbage treatment material according to claim 1,
wherein the kitchen garbage treatment material is constituted by organic matter only.

5. The kitchen garbage treatment material according to claim 1,
wherein the kitchen garbage treatment material contains a deodorizing material or an odor-removing material.

6. The kitchen garbage treatment material according to claim 1,
wherein the kitchen garbage treatment material contains an aromatic material.

7. The kitchen garbage treatment material according to claim 1,
wherein the sanitary product is a paper diaper.

8. A method for manufacturing a kitchen garbage treatment material that absorbs moisture contained in kitchen garbage, the method comprising:
a preparing step of preparing a water-absorbent material that is constituted by at least one of fluff pulp and water-absorbent polymer obtained by separating plastic from a sanitary product that contains the plastic, the fluff pulp, and the water-absorbent polymer; and
a forming step of forming the kitchen garbage treatment material that is constituted by a plurality of grains containing the water-absorbent material prepared in the preparing step,
wherein the grains include a granule that is obtained by granulating a granulating material that contains the water-absorbent material, and a coating portion that is provided so as to coat the granule and functions to bond the plurality of grains, which have absorbed moisture, to each other, and
wherein the plurality of grains include both a first grain and a second grain, wherein the coating portion of the first grain is thicker than the coating portion of the second grain such that a thickness of the coating portion of the second grain is 80% or less of a thickness of the coating portion of the first grain.

9. The kitchen garbage treatment material manufacturing method according to claim 8,
wherein the coating portion formed in the first coating step and the coating portion formed in the second coating step are constituted by a material of the same composition.

10. A method of treating kitchen garbage comprising:
causing the kitchen garbage treatment material according to claim 1 to absorb moisture contained in the kitchen garbage, by causing the kitchen garbage treatment material to come into contact with the kitchen garbage.

* * * * *